US006673749B1

(12) United States Patent
Singh et al.

(10) Patent No.: US 6,673,749 B1
(45) Date of Patent: Jan. 6, 2004

(54) USE OF PHYLLOCLADANE DITERPENOIDS FOR PLANT GROWTH PROMOTION AND ALLEVIATION OF GROWTH RETARDANT ALLELOCHEMICALS, AND METHOD THEREFOR

(75) Inventors: Anil Kumar Singh, Uttar Pradesh (IN); Guru Das Bagchi, Uttar Pradesh (IN); Sarita Singh, Uttar Pradesh (IN); Prem Dutt Dwivedi, Uttar Pradesh (IN); Anil Kumar Gupta, Uttar Pradesh (IN); Suman Preet Singh Khanuja, Uttar Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/335,104

(22) Filed: Dec. 31, 2002

(51) Int. Cl.$^7$ .......................... A01N 31/06; A01N 35/06
(52) U.S. Cl. ....................................... 504/348; 504/353
(58) Field of Search ................................... 504/348, 353

(56) References Cited

PUBLICATIONS

Hoagland. "Bioherbicides: Phytotoxic Natural Products". Chapter 7 in Agrochemical Discovery. ACS Symposium Serier 774, Baker et al, ed. p. 72–76. 2001.*

International Search Report of International Application No. PCT/IB02/05419, dated Apr. 8, 2003.

Pawan K. Agrawal et al., "Complete spectral assignment of calliterpenone by two–dimensional NMR techniques and carbon–13 NMR assignments for related phyllocladane diterpenoids" Database accession No. 125:168369 XP002233485 Abstract & Indian Journal of Chemistry, Section B: Organic Chemistry Including Medicinal Chemistry (1996) 35B(8) 803–805.

* cited by examiner

Primary Examiner—S. Mark Clardy
(74) Attorney, Agent, or Firm—Darby & Darby

(57) ABSTRACT

The present invention provides plant growth-promoting activities of natural plant active constituent calliterpenone and its derivatives belonging to the group phyllocladane diterpenoids. These phytochemicals and derivatives exhibit remarkable growth promoting activities on plant roots, shoots and promote seed germination both in monocotyledonous and dicotyledonous plants. These phytomolecules possess the antagonistic activity against allelochemicals of plant growth retardant nature and hence can be used to alleviate their detrimental effects.

13 Claims, No Drawings

USE OF PHYLLOCLADANE DITERPENOIDS FOR PLANT GROWTH PROMOTION AND ALLEVIATION OF GROWTH RETARDANT ALLELOCHEMICALS, AND METHOD THEREFOR

FIELD OF THE INVENTION

The present invention provides plant growth-promoting activities of natural plant active constituent, calliterpenone and its derivatives belonging to the group phyllocladane diterpenoids. These phytochemicals and derivatives exhibit remarkable growth promoting activities on plant roots, shoots and promote seed germination both in monocotyledonous and dicotyledonous plants. These phytomolecules also possess antagonistic activity against allelochemicals of plant growth retardant nature and hence can be used to alleviate their detrimental effects.

BACKGROUND OF THE INVENTION

Auxins and gibberellins are two main classes of natural compounds discovered simultaneously as plant growth stimulants. Besides these, cytokinins, abscisic acid, ethylene and many other compounds are also reported to possess plant growth regulatory properties. So far, more than 50 gibberellins have been discovered from natural sources. The growth stimulating activity has also been observed in several other types of natural plant constituents. Kaurenoic acid and steviol have been reported to be naturally occurring compounds having gibberellin like activity (Srivastava HS. 1999. Elements of Biochemistry. Rastogi Publications, Shivagi Road Merrut. Pp: 245–246). Helminthosporic acids isolated from Helminthosporium sativum and phaseolic acid isolated from the bean (Phaseolus species) seeds have also showed growth promoting activities. (Leopold A. C. and Kriedemann P. E. Plant Growth and Development Tata McGraw Hill Publishing Company Ltd., New Delhi. 137–140. 1981).

In recent years many papers and patents dealing with the plant growth promoting activities of natural and synthetic compounds have appeared. Important of them are salicilic acid (H S Gehlot et al. Advances in Plant Physiology Vol-I, 273–289, 1998), trioctanol(Ries et al, Science, 195 :1339, 1977) and other compounds reported from time to time. Goyal R. et al. reported three oxygenated alantolides from *Inula racemosa* (Phytochemistry 29(7) 2341–2343, 1990), three sesquiterpenoids, Saussureal, dehydrocostus lactone and costunolide isolated from *Saussurea lappa* have also shown growth promoting activities (I. P. Singh et al. Phytochemistry 31(7) 2529–2531, 1992 & K. K. Talwar et al. Phytochemistry 31 (1) 336–338 1992).

Among the synthetic derivatives, many compounds like triazoles, have been reported as a new group of promising plant growth promoters (R. P.Raghava et al. Advances in Plant Physiology, Vol-I 291–320, 1998). Various derivatives of organic acids reported to have plant growth promoting activity (e.g. West German Patent No. 1916054 discloses uses of α-hydroxy and α-ketoalkanoic acid having 7–10 carbon atoms and their derivatives; U.S. Pat. No. 3, 148,049 discloses growth promoting activity of certain halogenated keto acids under drought conditions). Mikami et al. (Agr Biol Chem 1970 3 4, 977–979) reported a number of hydroxy acids as plant growth regulators. Kamuro et al.(U.S. Pat. Nos. 6,093,683; 2000; 5,776,860; 1998; 4,846,877; 1989 and 6,271,176; 2001) described the derivatives of jasmonic acids as plant growth promoters. Danzig Morris J. et al. (U.S. Pat. No. 4,806,149; 1989) disclosed that monoxanthates and dixanthates of dipropylene glycol and triethylene glycol increase the growth and concentration of chlorophyll in plants.

Thus many active compounds have been reported so far to promote growth in plants. These compounds help in the increase in sizes of fruit, root, and shoot and in the total yield of the crop. However, it is difficult to obtain these compounds in great quantities from plants and cost to prepare them synthetically will be very high.

*Callicarpa macrophylla* Vahl. (Verbanaceae) is an erect shrub common to Indo-Gangetic plains and sub-Himalayan tracts from Kashmir to Assam ascending upto 2000 m. Leaves of plant are commonly used in rheumatism and aromatic root oil is given in stomach troubles. The plant has been investigated for its chemical constituents (Asolkar et al. Second supplement to Glossary of Indian Medicinal Plants with active principles, part 1. PID,CSIR, New Delhi, 155,1992).

The isolation of calliterpenone and its monoacetate from *Callicarpa macrophylla* was first reported by Chaterjee et al, Tetrahedron 28, 4319, 1972, and assigned the structure as 16α, 17 dihydroxy-ent kauan-II-one and its 17-acetate. Based on chemical and spectroscopic evidences, these structures were however, revised as 16α, 17 dihydroxy phyllocladan-3one and its 17-acetate on the basis further chemical 'H NMR, NOE and LIS and X-ray crystallographic data studies by Ahmad and Zaman (Tetrahedron Lett. 2179,1973), Fujita et al (Phytochemistry 14 1975 2249) and Wong et al (Acta Crystallography Sec. C 47 1991 906). Later, this compound was also isolated from some other species of the genus Callicarpa.

During previous studies on *Callicarpa macrophylla*, natural compounds 16α, 17 dihydroxy phyllocladan-3 one (calliterpenone), its 17-acetate (calliterpenone monoacetate) and two related minor constituents 16α, 17-isopropylidino 3-oxo phyllocladane (isopropylideno calliterpenone) and 30β, 16α, 17. trihydroxy phyllocladane (trihydroxy calliterpenone) werwe isolated and diacetate derivative of calliterpenone also prepared (Singh et al. Phytochemistry 37, 1994,587 and Indian Jour. of Chem.33B, 1994 1205). The complete spectral assignment of all the 5 phllocladane diterpenoids have also been done (Agarwal et al. Ind. Jour. of Chem.35B. 1996. 803–805).

SUMMARY OF THE INVENTION

The basis of the present invention is the finding that these pyllocladane diterpenoids when used in particular concentrations behave as growth promoters. Some of these compounds on certain dilutions produce more growth enhancement than that produced by $GA_3$ (Gibberellic acid) in identical conditions.

The invention also provides novel growth promoting activity of phyllocladane diterpenoids like calliterpenone and derivatives isolated from plants of *Callicarpa macrophylla* and their antagonizing effects against plant growth retardants.

Further the invention also provides the effective amount of phyllocladane diterpenoids selected from calliterpenone, calliterpenone mono-acetate, calliterpenone di-acetate, isopropylidino calliterpenone and tryhydroxy calliterpenone wherein 0.001 to 0.1 μM (w/v) concentrations of the said compounds can be used as sprays or in the media in tissue cultures or soaking of seeds, roots, shoots etc in said solutions.

The said solutions are prepared by dissolving required amount in minimum amount of water/organic solvents like ethyl alcohol, methanol, propenol followed by gentle warming and then the desired concentrations are achieved by adding suitable amount of distilled water.

DETAILED DESCRIPTION OF THE INVENTION

The present invention describes the growth promoting activities of phyllocladane diterpenoids isolated from the leaves of plant *Callicarpa macrophylla* that are not only cheap but show better activity at a particular dilution than the well known growth promoting hormone Gibberellic Acid ($GA_3$). In our experiment calliterpenone, its monoacetate and certain other derivatives naturally isolated from the plant *Callicarpa macrophylla* Vahl. (Verbanaceae) have shown promising growth promoting activities.

Calliterpenone(16α, 17 dihydroxy phyllocladan-3 one), a phyllocladane diterpenoid, is a stereoisomer of abbeokutone (16,17 dihydroxy kauran-3-one). Abbeokutone has kauranoid skeleton while calliterpenone has phyllocladane skeleton. The antagonistic activity of these phytoderivatives against negative allelochemicals makes their utility much higher as plant growth supporting chemicals.

As noted above the activity of phyllocladane diterpenoids used in the practice of this invention was observed when these compounds were tested for their effects on seed germination, root and shoot growth of certain plant species and their antagonistic effect on plant growth retardants by the method described by Bagchi G. D. et al Phytochemistry, 45(6)1131–1133, 1997.

Since the assay involves growing the plants/seedlings in aqueous solution, it demonstrates the usefulness of the process in promoting the growth of plants in hydroponics culture.

Like wise the process of this invention is also useful when plants are propagated by tissue culture or the solutions are sprayed on the plants. Further, these compounds may be utilized to antagonize the allelochemical effects produced by the preceding crops.

Phyllocladane diterpenoids of present invention are represented by general formula

|   |   | $R_1$ | $R_2$ | $R_3$ | Mol. For. | Mol. Wt. |
|---|---|---|---|---|---|---|
| 1 | Calliterpenone | H | H | O | $C_{20}H_{32}O_3$ | 320 |
| 2 | Calliterpenone monoacetate | H | Ac | O | $C_{22}H_{34}O_4$ | 362 |
| 3 | Calliterpone diacetate | Ac | Ac | O | $C_{24}H_{36}O_5$ | 404 |
| 4 | Isopropylideno calliterpenone | 1($RR_2$)=C($CH_3$)$_2$ | | O | $C_{23}H_{36}O_3$ | 360 |
| 5 | Trihydroxy phyllocladane | H | H | OH | $C_{20}H_{34}O$ | 322 |

The phyllocladane diterpenoids used in the process of present invention are seen to produce more than one type of growth regulatory effects on the plants. This effect on a plant depends on a number of variables including type of phyllocladane diterpenoid compounds used, their concentration, type of the plant species and the effective amount of the compound needed to obtain the desired response. The most suitable concentration for a particular application is readily determined by screening test as given in examples. Most, preferred phyllocladane diterpenoid are calliterpenone and calliterpenone mono-acetate and preferred concentration is 0.01 μM–0.00 μM.

The activity of phyllocladane diterpenoid used in practice of this invention was discovered when they were tested in two monocotyledonous and two dicotyledonous plants. Using general testing procedure as described earlier (Bagchi G. D. et al Phytochemistry, 45(6): 1131–1133, 1997). The test showed that different phyllocladane diterpenoids have growth promoting activities when used in concentrations between 0.1 μM and 0.001 μM (w/v basis), while on increasing the concentration, growth inhibitory activity was observed in certain cases.

For phyllocladane diterpenoid the optimum growth promoting concentration was 0.00 μM. The phyllocladane diterpenoids are generally useful in the practice of this invention are calliterpenone, calliterpenone mono-acetate, calliterpenone di-acetate, isopropylideno calliterpenone and trihydroxy calliterpenone. Solutions of the phyllocladane diterpenoids are conveniently applied to the plant in water added to the plant which may be prepared by dissolving the required amount in minimum amount of water/organic solvents like acetone or ethyl alcohol, methanol, propenol and followed by gentle warming and then the desired concentrations may be achieved by adding suitable amount of distilled water. Nutrients required by the plants may be added in the water. The solution of phyllocladane diterpenoid may be sprayed or roots, stems and seeds etc. may be soaked in it.

Phyllocladane diterpenoids, calliterpenone and calliterpenone monoacetate were obtained from the plant *Callicarpa macrophylla*, as described earlier (Singh and Agarwal. Phytochemistry 32(2) 587–588, 1994). other phyllocladane diterpenoids may be isolated from the plants or may be transformed chemically or microbially from naturally isolated calliterpenone (A. K.Singh and P. K.Agarwal. Indian Journal of Chemistry 33(B) 1205–1205,1994).

The invention is illustrated by following examples, which should not be constructed to limit the scope of present invention. The concentrations are given in micromolar solution, weight/volume basis.

Testing of Different Compounds

Plant growth promoting activity of calliterpenone, calliterpenone monoacetate, and calliterpenone di-acetate was examined at 0.1, 0.01 and 0.001 μM concentrations. The tests were conducted against seeds of two monocotyledonous (Hordeum vulgare and *Triticum aestivum*) and two dicotyledonous plants (*Vigna radiata* and *Trigonella foenum-graecum*). Control seeds were germinated in distilled water and all the observations were compared with $GA_3$ grown seedlings. The root and shoot growth of all the plant species were affected by the phyllocladane diterpenoids, although the extent of effect varied considerably in the plant species with the chemicals and their concentrations. In general, the growth promoting activities were more pronounced with dilute solutions, while the higher concentrations proved toxic to the species tested. Details of the procedure adopted and results obtained are discussed in the various examples.

EXAMPLE 1

To record the effect of phyllocladane diterpenoids on the growth of shoot, solutions of test compounds were prepared by following method-.

100 ml stalk solutions of 0.1 $\mu$M concentration were prepared by dissolving required amounts of various test compounds (depending upon their molecular weights) in minimum amount of ethanol or acetone and adding distilled water. From this stalk solution, 0.01 $\mu$M and 0.001 $\mu$M concentrations were prepared. Calliterpenone and calliterpenone di acetate was dissolved in 2.0 ml absolute ethanol (Merc), while; calliterpenone monoacetate, isopropylideno calliterpenone and trihydroxy calliterpenone were dissolved in 2.0 ml spectral grade acetone (Ranbaxy). The respective control test solutions of distilled water of each concentration also contained equal amount of absolute ethanol or acetone. For an assay, 10 seeds were placed on Whatman filter paper (moistened with 5.0 ml of test solution in a 9.0 cm diameter petridish (in triplicate). The pteridishes were incubated for 9 days in a germinator, maintained at 25.0±1.0° C. with 90% humidity and 4 hr light/day. At the end of incubation, observations were recorded on the seedlings in terms of germination, shoot and root growth. The data on the length of shoot and root of seedlings and number of seeds germinated in different concentrations of compounds were compared with the control, which was taken as 100%. The data thus obtained were presented in Table-1.

TABLE 1

Effect of phyllocladane diterpenoids on shoot growth of selected mono- and di- cotyledonous crop plants.

| | | Percent (%) shoot growth of seedlings in relation to control on 9$^{th}$ day after sowing in plant species | | | |
|---|---|---|---|---|---|
| Compounds | Concentration ($\mu$M) | Hordeum vulgare | Triticum aestivum | Vigna radiata | Trigonella foenum graecum |
| Calliterpenone | 0.1 | 102 | 95 | 128 | 121 |
| | 0.01 | 103 | 100 | 134 | 130 |
| | 0.001 | 118 | 105 | 121 | 121 |
| Calliterpenone Monoacetate | 0.1 | 118 | 109 | 123 | 133 |
| | 0.01 | 117 | 107 | 130 | 134 |
| | 0.001 | 113 | 106 | 138 | 135 |
| Calliterpenone Diacetate | 0.1 | 105 | 103 | 119 | 94 |
| | 0.01 | 106 | 106 | 115 | 121 |
| | 0.001 | 108 | 109 | 111 | 81 |
| Isopropylideno Calliterpenone | 0.1 | 108 | 102 | 145 | 100 |
| | 0.01 | 107 | 103 | 153 | 123 |
| | 0.001 | 106 | 103 | 89 | 137 |
| Trihydroxy Phyllocladane | 0.1 | 109 | 116 | 132 | 84 |
| | 0.01 | 108 | 112 | 145 | 72 |
| | 0.001 | 102 | 108 | 136 | 53 |
| GA$_3$ | 0.1 | 55 | 113 | 183 | 93 |
| | 0.01 | 91 | 115 | 196 | 112 |
| | 0.001 | 104 | 120 | 126 | 116 |

It is revealed from the table-1 that the solution of isopropylideno calliterpenone at 0.01 $\mu$M and 0.001 4 $\mu$M concentration produce maximum growth enhancement (i.e. 153% and 137% in relation to control) in the shoots of V.radiata and T. foenum-graecum respectively, Calliterpenone monoacetate exhibited slightly lower shoot growth enhancement in the above mentioned species (i.e. 138% and 135% respectively with 0.001 $\mu$M concentration). Calliterpenone and calliterpenone diacetate produced 134% and 119% enhancement in V.radiata and 130% and 121% enhancement in T. foenum-graecum in relation to control recording as 100% in shoot growth respectively. While trihydroxy phyllocladane, although enhanced the growth of V.radiata shoot maximum (145%) at 0.01M concentrations but it proved toxic to the shoots of T. foenum-graecum and reduced its growth at all dilutions tested. In other two species of monocots i.e. H.vulgare and T.aestivum, the effect was not much pronounced. All the solutions of compounds either enhanced the growth marginally or produced no significant effect on them. In V.radiata, however, all phyllocladane diterpenoids showed slightly better or equal growth-promoting activity to that of GA$_3$ (Table-1)

EXAMPLE 2

Root growth of seedlings was measured in the similar way as shoot growth from the experiment as described in Example 1.

Effect on Root Growth

Calliterpenone at 0.01 $\mu$M concentration produced maximum root growth (164% and 138%) enhancement in the roots of T. foenum-graecum and V.radiata respectively. While it produced 136% and 116% growth at 0.01 $\mu$M concentration in T.aestivum and H.vulgare as compared to the control. Calliterpenone monoacetate at 0.001 $\mu$M dilution produced maximum enhancement of growth in all four species tested ranging from 104%–141%. Iso-propylideno calliterpenone produced maximum growth at different concentrations in different species, 143% growth was observed in H.vulgare at 0.1 $\mu$M, followed by 132% growth in T. foenum-graecum at 0. 01 $\mu$M, while 109% enhancement in growth was recorded in T.aestivum at 0.001 $\mu$M concentration. Calliterpenone diacetate at 0.01 $\mu$M and 0.001 $\mu$M concentrations exhibited maximum (136% and 125%) enhancement in root growth in V.radiata and T.aestivum respectively, followed by 119% in H.vulgare and 113% in T. foenum-graecum at 0.01 $\mu$M and 0.001 $\mu$M concentrations respectively. Except H.vulgare, which showed 145% enhancement in growth of root, other tested species responded poorly to trihydroxy calliterpenone treatment. All the tested species produced better root growth by one or the other phyllocladane derivatives than GA$_3$.

TABLE 2

Effect of phyllocladane diterpenoids on root growth of selected mono- and dicotyledonous crop plants.

| | | Percent (%) root growth of seedlings in relation to control on 9$^{th}$ day after sowing in plant species. | | | |
|---|---|---|---|---|---|
| Compounds | Concentration ($\mu$M) | Hordeum vulgare | Triticum aestivum | Vigna radiata | Trigonella foenum graecum |
| Calliterpenone | 0.1 | 82 | 80 | 76 | 150 |
| | 0.01 | 116 | 80 | 138 | 164 |
| | 0.001 | 116 | 136 | 87 | 141 |
| Calliterpenone Monoacetate | 0.1 | 124 | 88 | 67 | 81 |
| | 0.01 | 114 | 102 | 85 | 95 |
| | 0.001 | 146 | 145 | 104 | 131 |
| Calliterpenone Diacetate | 0.1 | 98 | 103 | 93 | 95 |
| | 0.01 | 113 | 114 | 136 | 113 |
| | 0.001 | 119 | 125 | 91 | 73 |
| Isopropylideno Calliterpenone | 0.1 | 143 | 78 | 124 | 91 |
| | 0.01 | 115 | 107 | 131 | 123 |
| | 0.001 | 118 | 109 | 91 | 132 |
| Trihydroxy Phyllocladane | 0.1 | 106 | 111 | 93 | 82 |
| | 0.01 | 112 | 113 | 102 | 68 |
| | 0.001 | 145 | 90 | 100 | 55 |
| GA$_3$ | 0.1 | 70 | 62 | 104 | 45 |

TABLE 2-continued

Effect of phyllocladane diterpenoids on root growth of selected mono- and dicotyledonous crop plants.

| Compounds | Concentration ($\mu$M) | Percent (%) root growth of seedlings in relation to control on 9th day after sowing in plant species. | | | |
|---|---|---|---|---|---|
| | | Hordeum vulgare | Triticum aestivum | Vigna radiata | Trigonella foenum graecum |
| | 0.01 | 115 | 116 | 103 | 45 |
| | 0.001 | 132 | 131 | 102 | 123 |

EXAMPLE 3

Effect of test compounds on germination was observed from the same experiment as described in Example 1.

Effect on Seed Germination

Out of four species tested seeds two species i.e. *Vigna radiata* and *Trigonella foenum-graceum* exhibited some effect on their germination with three diterpenoids. Seed germination was 100–250% in *V.radiata* as compared to 100% in control and 200% in GA$_3$ treated seeds. The maximum germination (250%) was recorded in the seeds treated with 0.001 $\mu$M of calliterpenone. In *Trigonella foenum-graceum*, calliterpenone and its mono-acetate produced slightly better germination i.e. 113% as compared to 100% in control and GA$_3$ treated seeds. Other three diterpenoid, however, either retarded the germination (63%–88%) or produced no effect at different concentrations.

TABLE 3

Effect of phyllocladane diterpenoids on germination of seeds of selected mono- and dicotyledonous crop plants.

| Compounds | Concentration ($\mu$M) | Percent (%) germination of seeds in relation to control on 9th day after sowing in plant species | | | |
|---|---|---|---|---|---|
| | | Hordeum vulgare | Triticum aestivum | Vigna radiata | Trigonella foenum graecum |
| Calliterpenone | 0.1 | 100 | 100 | 150 | 113 |
| | 0.01 | 100 | 100 | 150 | 125 |
| | 0.001 | 100 | 100 | 250 | 113 |
| Calliterpenone Monoacetate | 0.1 | 100 | 100 | 200 | 113 |
| | 0.01 | 100 | 100 | 150 | 113 |
| | 0.001 | 100 | 100 | 100 | 113 |
| Calliterpenone Diacetate | 0.1 | 100 | 90 | 100 | 75 |
| | 0.01 | 100 | 100 | 100 | 100 |
| | 0.001 | 100 | 100 | 200 | 100 |
| Isopropylideno Calliterpenone | 0.1 | 100 | 100 | 100 | 100 |
| | 0.01 | 100 | 100 | 100 | 113 |
| | 0.001 | 100 | 100 | 150 | 100 |
| Trihydroxy Calliterpenone | 0.1 | 100 | 100 | 150 | 88 |
| | 0.01 | 100 | 100 | 150 | 75 |
| | 0.001 | 100 | 100 | 100 | 63 |
| GA$_3$ | 0.1 | 100 | 100 | 200 | 100 |
| | 0.01 | 100 | 100 | 200 | 100 |
| | 0.001 | 100 | 100 | 200 | 100 |

Based on above results it can be inferred that all the phyllocladane diterpenoids act as growth promoters at one or the other concentrations tested in almost all the species but the effects of calliterpenone and calliterpenone monoacetate were more pronounced in all experiments, i.e. root growth, shoot growth and seed germination. Therefore, more experiments with some different plant species were undertaken to confirm the above findings. Results obtained from example-4 confirm previous results and are described below

EXAMPLE 4

Effect of calliterpenone and its derivatives on seed germination and seedling growth in *Hibiscus sabdariffa* and *Sesbania cannabina* were measured in the similar way as these were measured in Example-1.

A. Effect of Calliterpenone (i) On root growth: Calliterpenone produced 157% enhancement in root growth in *Hibiscus sabdariffa* and 119% more root growth in *Sesbania cannabina* at the concentration of 0.001 $\mu$M as compared to their respective controls. When compared with the effect of GA$_3$ on root growth, it was observed that the effect of calliterpenone was even better than GA$_3$. This compound exhibited 134% and 109% more root growth in *H.sabdariffa* and *S.cannabina* respectively than GA$_3$ on 9$^{th}$ day of the experiment at 0.001 $\mu$M concentration as compared to GA$_3$ taken as 100%.

(ii) On shoot growth: In shoot growth, calliterpenone showed 182% and 120% enhancement in *H.sabdariffa* and *S. cannabina* seedling respectively as compared to their respective controls. This growth promoting activity was even better than GA$_3$.

Calliterpenone exhibited 110% and 104% more growth in *H.sabdariffa* and *S. cannabina* respectively as compared to GA$_3$ (100%) at 0.001 $\mu$M concentration.

(iii) On germination: Calliterpenone also showed enhanced effect on seed germination in *H.sabdariffa* and *S. cannabina*. In *H.sabdariffa*, there was 133% more germination, while in *S. cannabina* it was 150% more as compared to their respective controls at 0.001 $\mu$M concentration. When compared with GA$_3$, 133% and 150% increase was observed in *H.sabdariffa* and *S. cannabina* respectively at the same concentration.

B. Effect of Calliterpenone Monoacetate (i) On root growth: Calliterpenone mono acetate exhibited better activity in *S. cannabina* than *H.sabdariffa*. In *S. cannabina* it produced 114% more root growth than its control and also 143% more than GA$_3$ at 0.001 $\mu$M concentration.

(ii) On shoot growth: In shoot growth also calliterpenone mono-acetate was found more effective in *S.cannabina* than *H.sabdariffa*. In *S.cannabina* it produced 109% more growth than its control and when compared with GA$_3$ it was observed that this produced 1 16% more growth.

(iii) On germination: This compound did not produce any enhancement in germination in *H.sabdariffa* while it showed enhanced germination in *S.cannabina*. It produced 150% more germination as compared to its control and GA$_3$ treatments.

Information is Given in Tables 4 and 5

EXAMPLE 5

Alleviation of Growth Retardant Effect of Allelochemicals

The allelopathic relationship between different plant species is a well-established fact especially in crop plants.

*Artemisia annua* compounds reported to inhibit germination and growth of other species [Bagchi G. D. et al Phytochemistry, 45(6): 1131–1133, 1997]. An observation on extremely poor germination and almost no growth and ultimate death of *Hibiscus sabdariffa* seedlings grown in the field after the harvest of *Artemisia annua* plants prompted us for testing of allelopathic relationship between these two species.

Effect of A. Annua Seed Extracts on the Germination of *Hibiscus sabdariffa*

2.0 g, 1.5 g, 1.4 g, 1.2 g, 1.1 g, 1.0 g and 0.75 g seeds of *A.annua* were weighed and soaked in 50 ml distilled water each to prepare different concentration of the seed extract. After 24 hrs, extracts were filtered seeds and washed two times, with 15 ml distilled water and total extract was make up to 100 ml in a measuring flask by adding distilled water for each set and autoclaved. 10 seeds of *Hibiscus sabdariffa* in four replicates each in different seed extracts of *A. annua* were germinated in sterilized petridishes for 12 days as described in Example 1–4. Observations were compared with the control seeds germinated in distilled water in similar conditions. It was observed that the germination of *H. sabdariffa* seeds and mortality of its seedlings were directly proportional to the concentration of the seed extract. This clearly revealed that *A. annua* seeds produce allelopathic effect on plant species.

TABLE 6

Effect of different concentrations of *Artemisia annua* seed extracts on the survival of *Hibiscus sabdariffa* seedlings

| Concentrations of *A. annua* seed extract | Percent (%) mortality of *Hibiscus sabdariffa* seedlings after 12 days of germination as compared to the control (0%) |
| --- | --- |
| 0.75 g seeds/100 ml dw* | 47 |
| 1.0 g seeds/100 ml dw | 50 |
| 1.1 g seeds/100 ml dw | 52 |
| 1.2 g seeds/100 ml dw | 56 |
| 1.3 g seeds/100 ml dw | 69 |
| 1.4 g seeds/100 ml dw | 73 |
| 1.5 g seeds/100 ml dw | 88 |
| 2.0 g seeds/100 ml dw | 100 |

*dw distilled water

Table-6 clearly revealed that *A.annua* extract imparted adverse effect on seed germination and seedling growth ultimately producing mortality in plants. On the other hand, it is evident from Exp. 1–4 that phyllocladane diterpenenoids have produced germination and growth promoting activities on various plant species. To find out the combined effect of *A. annua* extract and phyllocladane diterpenoids on the germination and seedling growth of different plant species, 1:1 ratio of these compounds and *A.annua* extract were tested in the present experiment. For this, *Hibiscus sabdariffa* and *Sesbania cannabina* seeds were germinated in *A.annua* seed extract and solutions prepared by mixing this extract with 0.01 μm calliterpenone and calliterpenone mono-acetate respectively (Table 7). For the preparation of *A.annua* extract, 1.3 g seeds were soaked in 100 ml of distilled water for 24 hrs for testing on *H. sabdariffa*. Since, at this concentration, seeds of this species have shown 69% mortality which may be taken as good indicator. This effect was also recorded in *S.cannabina*. Since, in this case, seeds were almost half in weight as compared to the seeds of *H. sabdariffa*, accordingly, 0.65 g *A. annua* seeds were soaked in 100 ml of distilled water for 24 hrs to produce identical constraints in *S. cannabina*.

Effect on Seed Germination

For control, seeds were germinated in distilled water and all the observations were compared with it. *H. sabdariffa* and *S. cannabina* seeds exhibited 33% and 67% germination when grown in *A.annua* seed extract. However, when calliterpenone was mixed with *A.annua* extract in ratio 1:1 nullified the germination retarding effect of *A.annua* extract in *H. sabdariffa* seeds. While in *S. cannabina* it produced no improvement in seed germination. Calliterpenone monoacetate on the other hand when mixed with *A.annua* seed extract in 1:1 ratio, not only completely checked the inhibitory effect of *A.annua* extract in both *H.sabdariffa* and *S.cannabina* but also promoted shoot and root growth (Table-6). Therefore, calliterpenone and its derivatives can be used to nullify the effects of other growth retardants/allelochemicals in the fields for their reclamation.

TABLE 7

Antagonistic effect of calliterpenone and calliterpenone mono acetate with *Artemesia annua* seed extract.

| | Percent (%) germination and seedling growth in relation to control on the 9th day after sowing | | | | | |
| --- | --- | --- | --- | --- | --- | --- |
| | *Hibiscus sabdarifa cannabina* | | | *Sesbania* | | |
| | | Seedling growth | | | Seedling growth | |
| Treatments | Germination | Root | Stem | Germination | Root | Stem |
| *Artemisia annua* Extract | 33 | 0 | 0 | 67 | 0 | 0 |
| *Artemisia annua* Extract + 0.01 μm calliterpenone (50:50) | 100 | 150 | 130 | 67 | 225 | 144 |
| *Artemisia annua* | | | | | | |

TABLE 7-continued

Antagonistic effect of calliterpenone and calliterpenone mono acetate with *Artemesia annua* seed extract.

Percent (%) germination and seedling growth in relation to control on the 9<sup>th</sup> day after sowing

| | Hibiscus sabdarifa cannabina | | | Sesbania | | |
|---|---|---|---|---|---|---|
| | | Seedling growth | | | Seedling growth | |
| Treatments | Germination | Root | Stem | Germination | Root | Stem |
| Extract + 0.01 μm calliterpenone mono-acetate (50:50) | 100 | 172 | 169 | 100 | 175 | 138 |

Table 7 clearly revealed that Calliterpenone and Calliterpenone mono-acetate when mixed in 0.01 μm concentration at 1:1 ratio with *Artemisia annua* root water extract, it antagonized the growth retarding effects of extracts of *Artemisia annua* and produced better growth than the control (water soaked seeds). Calliterpenone produced 150% and 225% more growth in roots of *Hibiscus sabdariffa* and *Sesbania cannabina*. While calliterpenone mono-acetate produced 172% and 175% more growth respectively in roots of both species. Similarly 130% and 144% more growth was recorded in stems by calliterpenone in *Hibiscus sabdariffa* and *Sesbania cannabina* while by calliterpenone mono-acetate the growth was 169% and 175% in both the species respectively as compared to control taking as 100%.

TABLE 4

Effect of calliterpenone and calliterpenone mono-acetate on seed germination, shoot and root growth of *Hibiscus sabdariffa* and their comparison with GA₃.

| | | | Shoot growth | | | | | Root Growth (mm) | | | | |
|---|---|---|---|---|---|---|---|---|---|---|---|---|
| | Seed Ger. C | | 3<sup>rd</sup> Day C | | 6<sup>th</sup> Day C | | 9<sup>th</sup> Day C | | 3<sup>rd</sup> Day C | | 6<sup>th</sup> Day C | | 9<sup>th</sup> Day C |
| Conc. Of Calliterpenone | | | | | | | | | | | | |
| 0.1 μM | 2 | 0 | 13.6 | — | 52.5 | — | 72.5 | — | 14.0 | — | 21.5 | — | 23.0 | — |
| 0.01 μM | 2 | 2 | 39.8 | — | 78.0 | 36.8 | 85.0 | 41.6 | 17.0 | — | 19.2 | 14.0 | 25.8 | 19.6 |
| 0.001 μM | 4 | 3 | 27.1 | — | 61.0 | 41.0 | 94.6 | 52.0 | 12.6 | — | 28.6 | 14.6 | 33.4 | 21.3 |

| | | | Shoot growth | | | | | Root Growth (mm) | | | | |
|---|---|---|---|---|---|---|---|---|---|---|---|---|
| | Seed Ger. C | | 3<sup>rd</sup> Day C | | 6<sup>th</sup> Day C | | 9<sup>th</sup> Day C | | 3<sup>rd</sup> Day C | | 6<sup>th</sup> Day C | | 9<sup>th</sup> Day C |
| Conc. of C. mono-acetate | | | | | | | | | | | | |
| 0.1 μM | 0 | 2 | — | 20.0 | — | 40.0 | — | 40.0 | — | 4.0 | — | 7.0 | — | 19.0 |
| 0.01 μM | 2 | 4 | 33.5 | 36.2 | 67.5 | 66.9 | 75.2 | 94.7 | 17.5 | 20.2 | 18.3 | 22.9 | 21.3 | 30.3 |
| 0.001 μM | 3 | 5 | 28.8 | 85.8 | 85.8 | 105.0 | 91.6 | 131.1 | 16.3 | 20.3 | 19.3 | 27.9 | 24.8 | 35.0 |

| | | Shoot growth | | | Root Growth (mm) | | |
|---|---|---|---|---|---|---|---|
| | Seed Ger. | 3<sup>rd</sup> Day | 6<sup>th</sup> Day | 9<sup>th</sup> Day | 3<sup>rd</sup> Day | 6<sup>th</sup> Day | 9<sup>th</sup> Day |
| Conc. of GA₃ | | | | | | | |
| 0.1 μM | 2 | 46.8 | 76.6 | 81.6 | 15.3 | 29.3 | 32.0 |
| 0.01 μM | 3 | 39.6 | 76.5 | 76.5 | 15.8 | 16.6 | 16.6 |
| 0.001 μM | 3 | 47.6 | 76.3 | 85.8 | 21.5 | 22.8 | 25.0 |

TABLE 5

Effect of calliterpenone and calliterpenone mono-acetate on seed germination shoot and root growth of
Sesbania cannabina and their comparison with GA₃

| | Shoot growth | | | | | | | | Root Growth (mm) | | | | | |
|---|---|---|---|---|---|---|---|---|---|---|---|---|---|---|
| | Seed Ger. | C | 3rd Day | C | 6th Day | C | 9th Day | C | 3rd Day | C | 6th Day | C | 9th Day | C |
| Conc. Of Calliterpenone | | | | | | | | | | | | | | |
| 0.1 μM | 4 | 1 | 10.3 | 8.0 | 39.3 | 44.0 | 61.5 | 60.0 | 7.3 | 5.0 | 16.0 | 15.3 | 24.8 | 22.0 |
| 0.01 μM | 3 | 1 | 14.2 | 9.5 | 48.8 | 60.0 | 67.3 | 75.0 | 14.5 | 9.0 | 21.0 | 35.0 | 34.8 | 47.5 |
| 0.001 μM | 3 | 2 | 17.0 | 18.5 | 86.2 | 72.5 | 108.2 | 90.0 | 30.0 | 14.5 | 33.6 | 24.3 | 43.4 | 36.3 |

| | Shoot growth | | | | | | | | Root Growth (mm) | | | | | |
|---|---|---|---|---|---|---|---|---|---|---|---|---|---|---|
| | Seed Ger. | C | 3rd Day | C | 6th Day | C | 9th Day | C | 3rd Day | C | 6th Day | C | 9th Day | C |
| Conc. of C. mono-acetate | | | | | | | | | | | | | | |
| 0.1 μM | 2 | 2 | 11.0 | 39.8 | 50.0 | 105.0 | 66.0 | 117.5 | 5.5 | 29.5 | 7.5 | 32.5 | 23.0 | 47.5 |
| 0.01 μM | 3 | 2 | 20.0 | 20.1 | 57.8 | 66.1 | 78.2 | 80.0 | 28.3 | 19.7 | 28.4 | 25.0 | 45.1 | 56.9 |
| 0.001 μM | 3 | 1 | 44.0 | 0 | 110.0 | 4.0 | 120 | 110.0 | 40.0 | 0 | 40.0 | 9.0 | 57.0 | 50.0 |

| | Shoot growth | | | | Root Growth (mm) | | |
|---|---|---|---|---|---|---|---|
| | Seed Ger. | 3rd Day | 6th Day | 9th Day | 3rd Day | 6th Day | 9th Day |
| Conc. of GA₃ | | | | | | | |
| 0.1 μM | 1 | 32.5 | 42.3 | 61.3 | 16.5 | 16.6 | 26.6 |
| 0.01 μM | 2 | 27.0 | 66.8 | 67.0 | 23.5 | 25.5 | 27.8 |
| 0.001 μM | 1 | 31.0 | 85.6 | 103.6 | 35.5 | 34.0 | 40.0 |

C = growth in control

We claim:

1. A method for antagonizing the allelopathic effects of preceding crops comprising applying phyllocladane diterpenoids or solutions thereof on the seed/seedlings.

2. A method as claimed in claim 1 wherein the phyllocladane diterpenoids are selected from the group consisting of calliterpenone, calliterpenone monoacetate, calliterpenone diacetate, isopropylideno calliterpenone and trihydroxy calliterpenone.

3. A method as claimed in claim 2 wherein the phyllocladane diterpenoids are applied to the plants in aqueous solutions at concentrations ranging from 0.1 μM to 0.001 μM.

4. A method as claimed in claim 1 wherein the phyllocladane diterpenoids are isolated from the Callicarpa genera.

5. A method as claimed in claim 4 wherein the plant is *Callicarpa macrophylla*.

6. A method as claimed in claim 1 wherein the phyllocladane diterpenoides are applied to the plants after dissolving in minimal amount of water/solvent and diluting it to desire concentrations by adding water.

7. A method as claimed in claim 6 wherein the method of application is selected from spraying a solution of phyllocladane diterpenoides on crop plants, applying the solution on tissue culture or growing seedlings in the solution.

8. A method for plant growth promotion comprising applying to plants pyllocladane diterpenoids selected from the group consisting of calliterpenone, calliterpenone monoacetate, calliterpenone diacetate, isopropylideno calliterpenone and trihydroxy calliterpenone.

9. A method as claimed in claim 8 wherein the phyllocladane diterpenoids are applied to the plants in aqueous solutions at concentrations ranging from 0.1 μM to 0.001 μM.

10. A method as claimed in claim 9 wherein the phyllocladane diterpenoids are isolated from the Callicarpa genera.

11. A method as claimed in claim 10 wherein the plant is *Callicarpa macrophylla*.

12. A method as claimed in claim 8 wherein the phyllocladane diterpenoides are applied to the plants after dissolving in minimal amount of water/solvent and diluting it to desire concentrations by adding water.

13. A method as claimed in claim 12 wherein the method of application is selected from spraying a solution of phyllocladane diterpenoides on crop plants, applying the solution on tissue culture or growing seedlings in the solution.

* * * * *